US012648984B2

(12) United States Patent
Harti et al.

(10) Patent No.: US 12,648,984 B2
(45) Date of Patent: Jun. 9, 2026

(54) LONG TERM TREATMENT OF PSORIASIS

(71) Applicant: LEGACY HEALTHCARE (SWITZERLAND) SA, Epalinges (CH)

(72) Inventors: Saad Harti, Epalinges (CH); Nadine Vincent, Courbevoie (FR)

(73) Assignee: LEGACY HEALTHCARE (SWITZERLAND) SA, Epalinges (CH)

( * ) Notice: Subject to any disclaimer, the term of this patent is extended or adjusted under 35 U.S.C. 154(b) by 0 days.

(21) Appl. No.: 18/240,531

(22) Filed: Aug. 31, 2023

(65) Prior Publication Data

US 2025/0073299 A1     Mar. 6, 2025

(51) Int. Cl.
| | |
|---|---|
| *A61K 36/8962* | (2006.01) |
| *A61K 36/185* | (2006.01) |
| *A61K 36/752* | (2006.01) |
| *A61K 36/77* | (2006.01) |
| *A61P 17/06* | (2006.01) |

(52) U.S. Cl.
CPC ........ *A61K 36/8962* (2013.01); *A61K 36/185* (2013.01); *A61K 36/752* (2013.01); *A61K 36/77* (2013.01); *A61P 17/06* (2018.01)

(58) Field of Classification Search
None
See application file for complete search history.

(56) References Cited

FOREIGN PATENT DOCUMENTS

WO     WO 2012140013     * 10/2012

OTHER PUBLICATIONS

El Miedany Y, El Gaafary M, Youssef S, Almedany S, Palmer D. Using Simulation in Clinical Education: Psoriasis Area and Severity Index (PASI) Score Assessment. Curr Rheumatol Rev. 12(3):195-201 (2016).
Agozzino M, Noal C, Lacarrubba F, Ardigò M. Monitoring treatment response in psoriasis: current perspectives on the clinical utility of reflectance confocal microscopy. Psoriasis (Auckl). 20;7:27-34 (2017).

* cited by examiner

*Primary Examiner* — Michael V Meller
(74) *Attorney, Agent, or Firm* — Harness Dickey & Pierce P.L.C.

(57)     ABSTRACT

The invention relates to methods of treatment and/or prevention of an immune-mediated inflammatory skin disease in a subject, wherein the therapeutic effects persist for at least 24 weeks or more after the last administration of the composition. Also disclosed are kits and methods of treating and/or preventing an immune-mediated inflammatory skin disease using said composition.

16 Claims, 1 Drawing Sheet

FIG. 1B
FIB. 1A

LONG TERM TREATMENT OF PSORIASIS

FIELD OF THE INVENTION

The invention relates to methods of treatment and/or prevention of an immune-mediated inflammatory skin disease in a subject, wherein the therapeutic effects persist for at least 24 weeks or more after the last administration of the composition. Also disclosed are kits and methods of treating and/or preventing an immune-mediated inflammatory skin disease using said composition.

BACKGROUND OF THE INVENTION

Skin is our primary interface being in constant communication with the external environment, possessing a variety of defensive strategies. In addition to physical, microbiological, and chemical barriers, the skin harbors a highly specialized immunological niche crucial for the maintenance of tissue homeostasis, defense, and repair, in which resident immune cells, especially resident memory T cells (TRM) serve sentinel functions and contribute to long-lasting protective immunity against future immune challenges. These TRM cells, as well as the skin-infiltrating immune cells (including T cells) and non-immune cells appear to drive many inflammatory diseases of skin, such as psoriasis.

Psoriasis is a chronic long-lasting immune-mediated inflammatory skin disease (immunologic alterations in the skin) due to various factors, such as genetics, environmental triggers, cytokines and receptors, metabolism, cell signaling, transcription factors, non-coding RNAs, antimicrobial peptides, etc. According to the World Psoriasis Day consortium, more than 125 million people worldwide have psoriasis. The prevalence of psoriasis can vary across different regions and populations, reaching up to 3% of the total population. It can appear at any age, but often has two peaks of onset, i.e. between 20-30 and 50-60 years of age. The main locations of psoriasis are: scalp, palm, elbow, knees, and feet, nails, as well as skin folds/genitals. Psoriatic conditions are often associated with a significant impairment in life quality and a tremendous psychosocial burden along with an increased risk of cardiometabolic disease and even mortality in case of rare life-threatening psoriatic forms (e.g. generalized pustular and erythrodermic psoriasis).

Psoriatic skin conditions often occur alongside other autoimmune disorders, such as psoriatic arthritis, which is a type of arthritis that affects almost 1 in 3 people with psoriasis. It typically causes affected joints to become swollen, stiff and painful. Inflammation is major part of both psoriasis and psoriatic arthritis. Both conditions occur because the immune system mistakenly attacks the body's own healthy tissue.

Psoriasis is characterized by epidermal hyperplasia, abnormal differentiation of epidermal keratinocytes and dermal infiltration of inflammatory immune cells. The pathogenesis of psoriasis is complicated because of the complex interplay between immune cells, keratinocytes, and other skin-resident cells. In addition to the specific immunological components in the key psoriasis-driving pathogenic axis, for instance TNF-α, IL-23/IL-17, IL-12 and other molecules, immune T cells, in particular tissue-resident memory T (TRM) cells, play a crucial role in the pathogenesis of psoriasis.

Based on the understanding of multifactorial pathophysiology of psoriasis, multiple pathogenesis-oriented chemical drugs that target these molecules or cells to treat the disease have therefore been created. The currently available main treatments consist of: topical (e.g. corticosteroids); systemic (including oral immunosuppressants, e.g. methotrexate and cyclosporine and JAK inhibitors, as well as injectable biologic drugs, e.g. TNF blockers, IL-23/IL-17 inhibitors); and phototherapy (e.g. UVB). Biologics targeting TNF-α, IL-23, and IL-17 have shown remarkable success in the treatment of psoriasis. However, the side effects, safety, loss of efficacy and recurrence after drug discontinuation remain unaddressed. It should also be noted that long-term use of corticosteroids can lead to side effects such as skin thinning and increased risk of infections. Excessive/prolonged UV exposure can increase the risk of skin damage and skin cancer. Immunosuppressants and injectable biologic drugs may cause potential deleterious consequences, such as certain types of cancer and increased susceptibility to rare but life-threatening infections (e.g. progressive multifocal leukoencephalopathy (PML). Efalizumab (biologic agent approved for psoriasis) was voluntarily withdrawn by the FDA from the US market because of the risk of PML. More surprisingly, some therapeutic agents for the treatment of psoriasis (e.g. TNF inhibitors) are also known to have a paradoxical effect, either causing de novo psoriasis or aggravating preexisting psoriasis (from plaque psoriasis to pustular psoriasis and even erythroderma).

As no treatment is entirely remedial in their current form, and a limited but alarmingly growing proportion of patients with severe psoriasis are not responding satisfactorily to currently available modern treatments, emerging therapies aiming to develop novel treatment options with improved safety profiles are ongoing. Small-molecule drugs against phosphodiesterase 4 (PDE4), tyrosine kinase 2 (TYK2), as well as Gi protein-associated A3 adenosine receptor agonist have been and are being developed. Besides, stem cell and gene therapies also raise hopes for developing effective cure. However, these therapies are still under investigation and not widely accessible.

Facing the aforementioned unsolved long-term safety and efficacy issues, it is of imperative need to invent better treatment. The use of natural products or plants, which may have effective therapeutic characteristics and meanwhile demonstrate safety, will ensure long-term utilization by humans with few or no side effects. Indeed, numerous naturally derived compounds, such as natural antioxidants, anti-inflammatory or immunomodulatory agents have been proven to be the promising strategic options for future psoriasis treatments to deliver the life-changing potential for clear skin. For example, "Indigo naturalis" obtained from the *Baphicacanthus cusia* plants had been evaluated in 42 chronic plaque psoriasis patients in a randomized placebo-controlled experiment. It turned out that the indigo therapy alleviated symptoms by 81%, whereas the placebo therapy only reduced symptoms by 26%. There were no notable severe negative effects. Furthermore, punch biopsies revealed post-treatment normalization of epidermal appearance as well as a decrease in the main pro-inflammatory cytokine.

There is high unmet medical need for a treatment which is both, safe enough not to warrant drug holidays, and which efficacy persists beyond treatment interruption.

SUMMARY OF THE INVENTION

This object has been achieved by providing a method of treatment and/or prevention of an immune-mediated inflammatory skin disease in a subject, comprising administering a composition comprising, as active ingredients, effective amounts of an extract of *Allium* species, an extract of *Citrus* species, an extract of *Paullinia* species and an extract of *Theobroma* species, wherein the composition is administered topically for a period of time necessary to detect one or more therapeutic effects, and wherein the one or more therapeutic effects persist for at least 8 weeks, at least 12 weeks, at least 16 weeks, at least 20 weeks, at least 24 weeks or more after the last administration of the composition.

A further object of the present invention is to provide the use of a composition of the invention in the manufacture of a medicament for the treatment and/or prevention of an immune-mediated inflammatory skin disease in a subject.

A further object of the present invention is to provide a kit for the treatment and/or prevention of an immune-mediated inflammatory skin disease comprising a composition, or composition for use, of the invention.

BRIEF DESCRIPTION OF THE FIGURES

FIG. 1A-1B are pictures showing the effect of the topical application of a composition according to the invention (CG 428 lotion) for 6 months (1×/day) on the skin of a patient suffering from psoriasis. Left picture: before treatment (FIG. 1A); right picture: after 6 months of treatment (FIG. 1B).

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise/comprising" is generally used in the sense of include/including, that is to say permitting the presence of one or more features or components. The terms "comprise(s)" and "comprising" also encompass the more restricted ones "consist(s)", "consisting" as well as "consist/consisting essentially of", respectively.

As used in the specification and claims, the singular form "a", "an" and "the" include plural references unless the context clearly dictates otherwise.

As used herein the terms "subject"/"subject in need thereof", or "patient"/"patient in need thereof" are well-recognized in the art, and, are used interchangeably herein to refer to a mammal, including dog, cat, rat, mouse, monkey, cow, horse, goat, sheep, pig, camel, and, most preferably, a human. In some cases, the subject is a subject in need of treatment or a subject with a disease or disorder. However, in other aspects, the subject can be a normal subject. The term does not denote a particular age or sex. Thus, adult and newborn subjects, whether male or female, are intended to be covered. Preferably, the subject is a human, most preferably a human suffering from an immune-mediated inflammatory skin disease or a human that might be at risk of suffering from an immune-mediated inflammatory skin disease.

The term "about," particularly in reference to a given quantity, number or percentage, is meant to encompass deviations of plus or minus ten percent (±10). For example, about 5% encompasses any value between 4.5% to 5.5%, such as 4.5, 4.6, 4.7, 4.8, 4.9, 5, 4.1, 5.2, 5.3, 5.4, or 5.5.

As used herein, "at least one" means "one or more", "two or more", "three or more", etc. For example, at least 8 weeks means 8 weeks or more i.e., 9 weeks, 10 weeks, 11 weeks.

The present invention further contemplates methods of treatment and/or prevention of an immune-mediated inflammatory skin disease in a subject.

In one aspect, the methods of treatment and/or prevention of an immune-mediated inflammatory skin disease in a subject comprises, administering a composition comprising, as active ingredients, effective amounts of an extract of *Allium* species, an extract of *Citrus* species, an extract of *Paullinia* species and an extract of *Theobroma* species, wherein the composition is administered topically for a period of time necessary to detect one or more therapeutic effects.

In one aspect, the one or more therapeutic effects persist for at least 8 weeks, at least 12 weeks, at least 16 weeks, at least 20 weeks, at least 24 weeks or more after the last administration of the composition.

In one aspect, the methods of treatment and/or prevention of an immune-mediated inflammatory skin disease further comprise administering a combination therapy, either simultaneously or separately.

Where the disease is psoriasis, the combination therapy essentially consists of an additional therapeutic agent selected from the group comprising topicals (vitamin D3 analogs and corticosteroids), phototherapy with UVB or UVA, photochemotherapy (Psoralen+UVA), systemic treatments and biologics.

The term "treatment" or "treating" means any administration of a composition, pharmaceutical composition, therapeutic agent, active ingredient, compound, etc., of the disclosure to a subject for the purpose of:

(i) inhibiting the disease, that is, arresting the development of clinical symptoms;

(ii) reversing the disease, and/or (iii) relieving the disease, that is, causing the regression of clinical symptoms.

As used herein, the term "prevention" or "preventing" means any administration of a composition, pharmaceutical composition, therapeutic agent, active ingredient, compound, etc. . . . , of the disclosure to a subject for the purpose of preventing the disease, that is, causing the clinical symptoms and signs of the disease not to develop.

In the context of the present invention, the disease is an immune-mediated inflammatory skin disease. In an aspect, the immune-mediated inflammatory skin disease is selected from the group comprising psoriasis, systemic sclerosis, dermatomyositis, vitiligo, and lichen sclerosus, or a combination of one or more thereof. Preferably, the immune-mediated inflammatory skin disease is psoriasis. Non-limiting examples of psoriasis comprise chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA).

The most common type of psoriasis is the plaque type, affecting up to 80 percent of patients. Plaques can appear anywhere on the body as marked by patches of inflamed, itchy, and painful skin with scales. The skin may be red with silvery-white scales, and the plaques may look purple. Eruptive (guttate) psoriasis affects roughly 8 percent of psoriatic patients. It may occur occasionally after strepto-coccal infection. Inverse psoriasis affects one out of four patients who have inflamed deep-red or darkened smooth skin. It often appears in skin folds of the body (e.g. under-arms, under breasts) and can cause severe itching and pain. Pustular psoriasis affects about 3% of psoriasis patients. Symptoms include pustules (white, pus-filled, painful bumps) that may be surrounded by inflamed or reddened or discolored skin. About 2% of people living with psoriasis have erythrodermic psoriasis, that is associated with severe itching and pain, changes in heart rate and temperature, dehydration and nail changes. Although rare, it can cause intense redness or discoloration and shedding of skin layers in large sheets, often affecting nearly the whole body and can be life-threatening.

More preferably, the psoriasis is chronic plaque type.

The term "effective amount" as used herein means a therapeutically effective amount of a composition, a phar-maceutical composition, a therapeutic agent, an active ingre-dient, a compound, etc of the disclosure, high enough to significantly positively modify the symptoms and/or condi-tion to be treated, but low enough to avoid serious side effects (at a reasonable risk/benefit ratio), within the scope of sound medical judgment.

In the context of the present invention, the composition of the invention comprises, as active ingredients, effective amounts of an extract of *Allium* species, an extract of *Citrus* species, an extract of *Paullinia* species and an extract of *Theobroma* species active *Allium* species, an extract of *Citrus* species, an extract of *Paullinia* species and an extract of *Theobroma* species.

The term extract, or aqueous-alcoholic extract, of *Allium* species refers particularly to aqueous-alcoholic extracts and native extracts, e.g. aqueous extract, obtained from all species of the genus *Allium* (family Liliaceae) and especially *Allium cepa*.

The term extract, or aqueous-alcoholic extract, of *Citrus* species refers particularly to aqueous-alcoholic extracts and native extracts e.g. aqueous extracts, obtained from all species of the genus *Citrus* (family Rutaceae) and especially *Citrus limon*.

The term extract (atomised or not), or aqueous-alcoholic extract, of *Paullinia* species refers particularly to aqueous-alcoholic extracts and native extracts, e.g. aqueous extracts, obtained from all species of the genus *Paullinia* (family Sapindaceae) and especially *Paullinia cupana*.

The term extract (atomised or not), or aqueous-alcoholic extract, of *Theobroma* species refers particularly to aqueous-alcoholic extracts and native extracts, e.g. aqueous extracts, obtained from all species of the genus *Theobroma* (family Malvaceae) and especially *Theobroma cacao*.

In an aspect of the invention, the composition of the invention is administered topically, usually on external skin surface preferably to an affected area for a period of time necessary to detect one or more therapeutic effects consist-ing of slowing down or arresting the development of clinical symptoms, reversing the disease and/or causing the regres-sion of clinical symptoms.

In one aspect, clinical symptoms of psoriasis comprise:

plaques that can appear anywhere on the body as marked by patches of inflamed, itchy, and painful skin with scales. The skin may be red with silvery-white scales, and the plaques may look purple (e.g. in Plaque pso-riasis), eruptions that may occur occasionally after streptococcal infection (e.g. Eruptive (guttate) psoriasis), pustules (white, pus-filled, painful bumps) that may be surrounded by inflamed or reddened or discolored skin (e.g. Inverse psoriasis)

severe itching and pain, changes in heart rate and tem-perature, dehydration and nail changes (e.g. erythro-dermic psoriasis).

The period of time necessary to detect one or more therapeutic effects is usually comprised between about 16 to about 48 weeks, preferably between about 20 to about 40 weeks, more preferably between about 20 and about 32 weeks and even more preferably about 24 weeks.

Any invasive or non-invasive method known in the art may be used to detect, monitor and/or evidence the one or more therapeutic effects described above.

In one aspect, the one or more therapeutic effects are detected, monitored and/or evidenced by:

skin histology, defining a PASI (Psoriasis Area Severity Index) score (where the disease is psoriasis), that is a tool used to measure the severity and extent of psoriasis (El Miedany Y. et al., 2016), using reflectance confocal microscopy (RCM) (Agozzino M, et al., 2017).

In one aspect, a decrease or regression of at least about 2% or more, at least about 5% or more, at least about 10% or more, at least about 15% or more, at least about 20% or more, at least about 30% or more, at least about 40% or more, or at least about 50% or more of the clinical symptoms detected when compared to the subject's symptoms deter-mined before starting the administration of the composition and indicates that the administration of the composition of the invention is effective.

A decrease of at least about 2% or more, at least about 5% or more, at least about 10% or more, at least about 15% or more, at least about 20% or more, at least about 30% or more, at least about 40% or more, or at least about 50% or more of the clinical symptoms detected when compared to the subject's symptoms determined after the last adminis-tration of the composition, indicates that one or more therapeutic effects are detected and persist after the stop of said topical administration.

In some aspects, the one or more therapeutic effects persist and even improves over the time.

Usually, the composition of the invention is administered topically, preferably on external skin surface of an affected area, at least once per day, at least twice per day, or more. More preferably, the composition of the invention is admin-istered topically once per day.

Usually, a volume comprised between about 0.5 ml and 2.5 ml is applied, at least once per day, at least twice per day, or more, in order to cover the whole affected area of the subject.

In one aspect, the composition of the invention comprises from about 65% to about 93% by weight of an aqueous or aqueous-alcoholic extract of *Allium* species; from about 5% to about 33% by weight of an aqueous or aqueous-alcoholic extract of *Citrus* species; from about 0.25% to about 2.5% by weight of an aqueous or aqueous-alcoholic extract of

*Paullinia* species; and from about 0.25% to about 2.5% by weight of an aqueous or aqueous-alcoholic extract of *Theobroma* species.

In a preferred aspect, the composition of the invention comprises from about 65% to about 93% by weight of an aqueous or aqueous-alcoholic extract of *Allium cepa*; from about 5% to about 33% by weight of an aqueous or aqueous-alcoholic extract of *Citrus limon*; from about 0.25% to about 2.5% by weight of an aqueous or aqueous-alcoholic extract of *Paullinia cupana*; and from about 0.25% to about 2.5% by weight of an aqueous or aqueous-alcoholic extract of *Theobroma cacao*.

In an even more preferred aspect, the composition of the invention comprises about 87% by weight of an aqueous or aqueous-alcoholic extract of *Allium cepa*; about 12% by weight of an aqueous or aqueous-alcoholic extract of *Citrus limon*; about 0.33% by weight of an aqueous or aqueous-alcoholic extract of *Paullinia cupana*; and about 0.33% by weight of an aqueous or aqueous-alcoholic extract of *Theobroma cacao*.

In one aspect, the composition of the invention further contains as excipients from about 0.05% to about 8.0% by weight of sodium chloride and from about 1% to about 40% by weight of glycerine, based on the total weight of the composition.

In one aspect, the composition of the invention comprises from about 0.05% to about 8.0%, preferably from about 0.1% to about 7.0%, more preferably from about 0.4% to about 6.0%, and even more preferably from about 0.9% to about 3% by weight of sodium chloride, based on the total weight of the composition.

In one aspect, the composition of the invention comprises from about 1% to about 40%, preferably from about 1.2% to about 20%, more preferably from about 1.8% to about 15% by weight of glycerine, based on the total weight of the composition.

The compositions of the invention suitable for topical administration include liquid or semi-liquid preparations suitable for penetration through the skin such as solutions, lotions, shake lotions, creams, ointments, gels, foams, transdermal patches, powders, solids, sponges, tapes, vapors, pastes, tinctures, microparticles, microcapsules, nanoparticles, liposomes, or emulsions. Preferably, the compositions of the invention suitable for topical administration are in the form of solutions or lotions.

In one aspect, the compositions of the invention are combined or co-administered with an additional therapeutic agent.

Where the disease is psoriasis, the additional therapeutic agent is selected from the group comprising topicals (vitamin D3 analogs and corticosteroids), phototherapy with UVB or UVA, photochemotherapy (Psoralen+UVA), systemic treatments and biologics.

The present invention further contemplates the use of a composition of the invention in the manufacture of a medicament for the treatment and/or prevention of an immune-mediated inflammatory skin disease in a subject, comprising, administering the medicament comprising, as active ingredients, effective amounts of an extract of *Allium* species, an extract of *Citrus* species, an extract of *Paullinia* species and an extract of *Theobroma* species, wherein the composition is administered topically for a period of time necessary to detect one or more therapeutic effects.

In one aspect, the one or more therapeutic effects persist for at least 8 weeks, at least 12 weeks, at least 16 weeks, at least 20 weeks, at least 24 weeks or more after the last administration of the composition.

The invention also contemplates kits for the treatment and/or prevention of an immune-mediated inflammatory skin disease as described herein. In one aspect of the invention, the kit comprises a composition, or composition for use, of the invention.

The kits of the invention may also comprise a container and a label or package insert on or associated with the container. Suitable containers include, for example, bottles, vials, syringes, dispensers, a spray applicator, etc. The containers may be formed from a variety of materials such as glass or plastic.

The label or package insert may comprise instructions for use thereof. Instructions included may be affixed to packaging material or may be included as a package insert. While the instructions are typically written or printed materials they are not limited to such. Any medium capable of storing such instructions and communicating them to an end user is contemplated by this disclosure.

The present disclosure is to be considered as in all aspects illustrated and not restrictive, the scope of the invention being indicated by the appended Claims, and all changes which come within the meaning and range of equivalency are intended to be embraced therein.

EXAMPLES

Material and Methods

The composition has been evaluated in one patient case. A 61 year old men, presenting extensive plaque psoriasis on the trunk for several years (illustration 1), was regularly treated with UVA, then hydrocortisone, then Acitretine. The treatments reduced redness, but never the psoriasis itself. Upon cessation of the above-mentioned treatment, redness came back.

He was provided with the composition according to the invention to apply once daily on the whole trunk. No concomitant treatment for psoriasis or else was used.

Results

After 6 months of once-daily application, the psoriasis plaques merely disappeared and took a circinate shape (illustration 2). The circinate shape is suggestive of a cure of the disease (Nicolas et al., 1999). After 6 months, treatment with the composition was discontinued. Several months after discontinuation, the patient was questioned regarding the status of the disease. No disease relapse was reported.

REFERENCES

Nicolas J F, Thivolet J. Psoriasis; de la clinique à la thérapeutique. John Libbey J D Book Series. 26 Aug. 1998

Agozzino M, Noal C, Lacarrubba F, Ardigò M. Monitoring treatment response in psoriasis: current perspectives on the clinical utility of reflectance confocal microscopy. Psoriasis (Auckl). 2017 Feb. 20; 7:27-34.

El Miedany Y, El Gaafary M, Youssef S, Almedany S, Palmer D. Using Simulation in Clinical Education: Psoriasis Area and Severity Index (PASI) Score Assessment. Curr Rheumatol Rev. 2016; 12 (3): 195-201.

The invention claimed is:

1. A method of treatment of psoriasis in a human in need thereof consisting essentially of topically administering a composition to the human, wherein the composition consists of, as active ingredients, effective amounts of an extract of

*Allium* species, an extract of *Citrus* species, an extract of *Theobroma* species, and an extract of *Paullinia* species, and excipients, wherein the extract of *Paullinia* species consists of an aqueous extract without alcohol, and wherein one or more therapeutic effects of the treatment persists for at least 8 weeks after the last administration of the composition.

2. The method of treatment according to claim 1, wherein the psoriasis is selected from the group consisting of chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA).

3. The method of treatment according to claim 1, wherein a decrease or regression of at least about 2% or more, at least about 5% or more, at least about 10% or more, at least about 15% or more, at least about 20% or more, at least about 30% or more, at least about 40% or more, or at least about 50% or more of the clinical symptoms is detected when compared to the human's symptoms determined before starting the administration of the composition.

4. The method of treatment according to claim 1, wherein a decrease or regression of at least about 2% or more, at least about 5% or more, at least about 10% or more, at least about 15% or more, at least about 20% or more, at least about 30% or more, at least about 40% or more, or at least about 50% or more of the clinical symptoms is detected when compared to the human's symptoms determined after the last administration of the composition.

5. The method of treatment according to claim 1, wherein the composition consists essentially of from about 65% to about 93% by weight of an aqueous or aqueous-alcoholic extract of *Allium* species; from about 5% to about 33% by weight of an aqueous or aqueous-alcoholic extract of *Citrus* species; from about 0.25% to about 2.5% by weight of an aqueous extract of *Paullinia* species; and from about 0.25% to about 2.5% by weight of an aqueous or aqueous-alcoholic extract of *Theobroma* species.

6. The method of treatment according to claim 1, wherein the composition consists essentially of from about 65% to about 93% by weight of an aqueous or aqueous-alcoholic extract of *Allium cepa*; from about 5% to about 33% by weight of an aqueous or aqueous-alcoholic extract of *Citrus limon*; from about 0.25% to about 2.5% by weight of an aqueous extract of *Paullinia cupana*; and from about 0.25% to about 2.5% by weight of an aqueous or aqueous-alcoholic extract of *Theobroma cacao*.

7. The method of treatment according to claim 6, wherein the composition consists essentially of about 87% by weight of an aqueous or aqueous-alcoholic extract of *Allium cepa*; about 12% by weight of an aqueous or aqueous-alcoholic extract of *Citrus limon*; about 0.33% by weight of an aqueous extract of *Paullinia cupana*; and about 0.33% by weight of an aqueous or aqueous-alcoholic extract of *Theobroma cacao*.

8. The method of treatment according to claim 1, wherein the composition further consists essentially of sodium chloride and glycerine.

9. The method of treatment according to claim 8, wherein the composition consists essentially of from about 0.05% to about 8.0%, from about 0.1% to about 7.0%, or from about 0.4% to about 6.0% by weight of sodium chloride, based on the total weight of the composition.

10. The method of treatment according to claim 9, wherein the composition consists essentially of from about 1% to about 40%, from about 1.2% to about 20%, or from about 1.8% to about 15% by weight of glycerine, based on the total weight of the composition.

11. The method of treatment according to claim 1, wherein the composition is administered topically on the skin of the human to an affected area of the human.

12. The method of treatment according to claim 1, wherein the composition is administered at least once a day.

13. The method of treatment according to claim 1, wherein the composition is administered for about 16 to 48 weeks.

14. The method of treatment according to claim 13, wherein the composition is administered for about 20 to 40 weeks.

15. The method of treatment according to claim 1, wherein the one or more therapeutic effects of the treatment persists for at least 12 weeks after the last administration of the composition.

16. The method of treatment according to claim 15, wherein the one or more therapeutic effects of the treatment persists for at least 16 weeks after the last administration of the composition.

* * * * *